(12) United States Patent
Jeong et al.

(10) Patent No.: US 8,133,179 B2
(45) Date of Patent: Mar. 13, 2012

(54) METHOD OF DISPLAYING AN ELASTIC IMAGE

(75) Inventors: Mok Kun Jeong, Seoul (KR); Ra Young Yoon, Seoul (KR)

(73) Assignee: Medison Co., Ltd., Hongchun-gun (KR)

( * ) Notice: Subject to any disclaimer, the term of this patent is extended or adjusted under 35 U.S.C. 154(b) by 1168 days.

(21) Appl. No.: 11/854,202

(22) Filed: Sep. 12, 2007

(65) Prior Publication Data

US 2008/0064956 A1 Mar. 13, 2008

(30) Foreign Application Priority Data

Sep. 13, 2006 (KR) .................. 10-2006-0088547

(51) Int. Cl.
*A61B 8/00* (2006.01)
(52) U.S. Cl. .................. 600/438; 600/437; 600/443
(58) Field of Classification Search .................. 600/437, 600/438, 440, 441, 443
See application file for complete search history.

(56) References Cited

U.S. PATENT DOCUMENTS

| | | | | |
|---|---|---|---|---|
| 6,270,459 | B1 * | 8/2001 | Konofagou et al. | 600/449 |
| 6,508,768 | B1 * | 1/2003 | Hall et al. | 600/443 |
| 6,558,324 | B1 * | 5/2003 | Von Behren et al. | 600/440 |
| 2004/0210136 | A1 * | 10/2004 | Varghese et al. | 600/443 |
| 2005/0251034 | A1 * | 11/2005 | Dubberstein | 600/437 |
| 2006/0285731 | A1 | 12/2006 | Jiang et al. | |
| 2008/0071174 | A1 * | 3/2008 | Waki et al. | 600/442 |
| 2008/0269606 | A1 * | 10/2008 | Matsumura | 600/438 |

FOREIGN PATENT DOCUMENTS

| | | |
|---|---|---|
| EP | 1 762 180 A1 | 3/2007 |
| WO | WO 2005/120358 A1 | 12/2005 |

* cited by examiner

*Primary Examiner* — Brian Casler
*Assistant Examiner* — Amanda Lauritzen
(74) *Attorney, Agent, or Firm* — Oblon, Spivak, McClelland, Maier & Neustadt, L.L.P.

(57) ABSTRACT

A method of displaying an elastic image, comprising: a) performing transmission/reception of an ultrasound signal along a plurality of scan lines set on a target object to obtain first ultrasound data, the target object including a plurality of tissues; b) performing transmission/reception of an ultrasound signal along a plurality of scan lines set on the target object by applying a stress to the target object to obtain second ultrasound data; c) calculating displacements of the tissues based on the first and second ultrasound data; d) calculating strains in the tissues based on the calculated displacements; e) forming an elastic image based on the calculated strains and a graph indicating changes of the tissues for the respective scan lines; and f) displaying the elastic image together with the graph.

9 Claims, 10 Drawing Sheets

METHOD OF DISPLAYING AN ELASTIC IMAGE

The present application claims priority from Korean Patent Application No. 10-2006-0088547 filed on Sep. 13, 2006, the entire subject matter of which is incorporated herein by reference.

BACKGROUND

1. Field

The present invention generally relates to an ultrasound system, and more particularly to a method of displaying an elastic image in the ultrasound system.

2. Background

An ultrasound system has become an important and popular diagnostic tool since it has a wide range of applications. Specifically, due to its non-invasive and non-destructive nature, the ultrasound system has been extensively used in the medical profession. Modern high-performance ultrasound systems and techniques are commonly used to produce two or three-dimensional images of internal features of an object (e.g., human organs).

The ultrasound system generally uses a probe containing a wide bandwidth transducer to transmit and receive ultrasound signals. The ultrasound system forms images of human internal tissues by electrically exciting an acoustic transducer element or an array of acoustic transducer elements to generate ultrasound signals that travel into the body. The ultrasound signals produce ultrasound echo signals since they are reflected from body tissues, which appear as discontinuities to the propagating ultrasound signals. Various ultrasound echo signals return to the transducer element and are converted into electrical signals, which are amplified and processed to produce ultrasound data for an image of the tissues.

Generally, the ultrasound image is displayed in a Brightness-mode (B-mode) by using reflectivity caused by an acoustic impedance difference between the tissues of the target object. However, if the reflectivity of the target object is hardly different from those of the neighboring tissues such as tumor, cancer or the like, then it is not easy to recognize the target object in the B-mode image. Further, an ultrasound elastic imaging technology has been developed to display an image of the target object by using mechanical characteristics of the target object. Such technology is very helpful for diagnosing lesions such as cancers. The tumor or cancer is relatively stiffer than the neighboring tissues. Thus, when stress is uniformly applied, a variation of the tumor or cancer is typically smaller than those of the neighboring tissues.

An elasticity of a tissue is measured by using ultrasound data obtained before and after compressing the tissue. A compression plate mounted on an ultrasound probe is used to compress the tissue. A user may press the compression plate on the target object, thereby compressing the tissues of the target object. In such a case, strain in the tissues depends on the pressure applied by the user. The quality of an elastic image may be changed according to the pressure applied to the tissue. For example, if the pressure is relatively weak, then a difference in strain between the tumor or cancer tissue and the neighboring tissues thereof tends to be very small, while the tumor or cancer is hardly distinguishable from the neighboring tissues in the elastic image.

Further, if the pressure is relatively hard, then a correlation between the tumor or cancer tissue and the neighboring tissues becomes lowered. This is so that the quality of the elastic image can be deteriorated. Therefore, an appropriate pressure is required to obtain an enhanced elastic image. Experimentally, when the strain of the tissues falls within a range of 0.5-3%, an optimal elastic image can be obtained. The pressure may be applied in a different power according to the user or measure time. Therefore, there is a need to provide indices indicating how hard the pressure is applied so as to obtain an enhanced elastic image in the ultrasound system.

BRIEF DESCRIPTION OF THE DRAWINGS

Arrangements and embodiments may be described in detail with reference to the following drawings in which like reference numerals refer to like elements and wherein.

DETAILED DESCRIPTION

Figure 1:
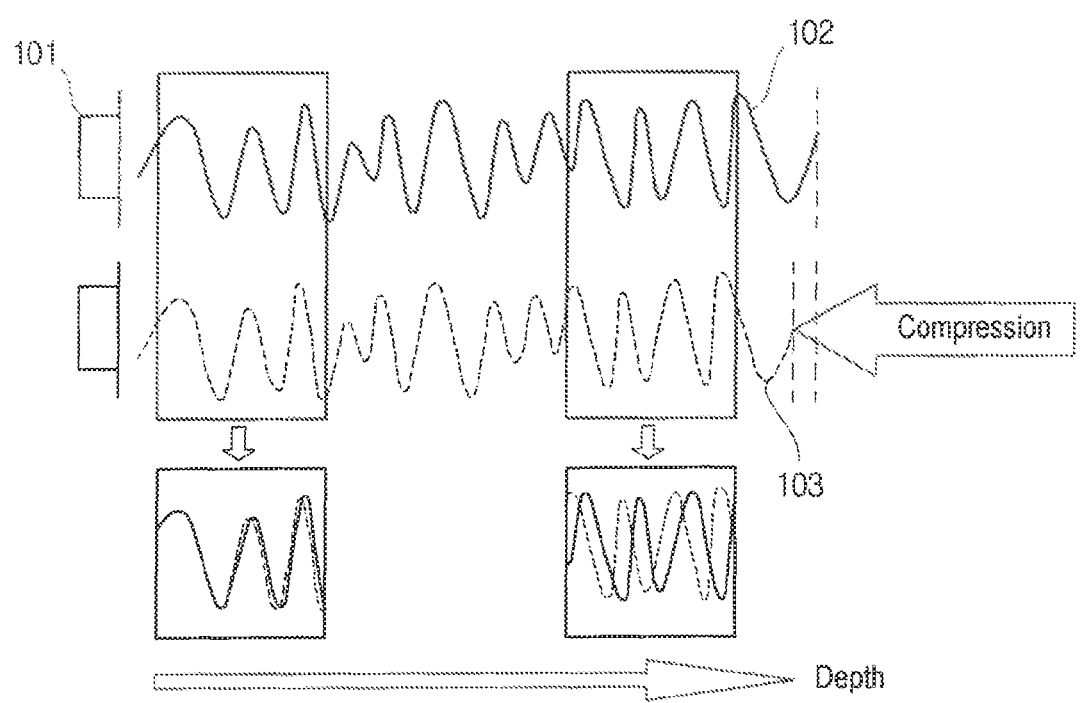
FIG. 1 shows waveforms of ultrasound signals before and after applying a stress to a target object.

FIG. 1 shows waveforms of ultrasound signals before and after applying a stress to a target object. An ultrasound signal is transmitted to a target object without applying any stress to the target object to obtain a first receive signal 102. Then, an ultrasound signal is transmitted to the target object by applying the stress to obtain a second receive signal 103. The stress may be applied by using an ultrasound probe.

When a pressure is applied to the target object, tissues in the target object, which correspond to reflectors of the ultrasound signal, move toward a pressing direction. Due to this movement of the reflectors, a variation between waveforms of ultrasound receive signals obtained with and without the application of the pressure may occur. A displacement of tissues may be calculated by using the variation. Since the displacement may be changed according to the stiffness of the tissues, the displacement reflects the characteristics of the tissues.

As shown in FIG. 1, a variation of ultrasound receive signals 102 and 103 is relatively small at a location near a transducer element 101, while a variation is relatively large at a location far away from the transducer element 101 due to the accumulation of the variation in a depth direction.

If a pressure is uniformly applied to the tissues in one direction, then the tissues are differently deformed according to the stiffness thereof. After obtaining a displacement function for the deformed tissues, the displacement function may be differentiated to obtain a gradient representing a strain of the deformed tissues. The strain is used to form an elastic image.

The displacement for calculating the strain may be determined through cross correlation or autocorrelation for RF data or baseband IQ data. Generally, since the RF data or the IQ data are sampling data obtained by sampling ultrasound receive signals in a sampling interval, it is difficult to calculate an accurate displacement. Therefore, in order to calculate the accurate displacement in accordance with one embodiment of the present invention, a coarse displacement is calculated from the sampling data in a sampling interval unit and then the sampling data are interpolated. Thereafter, a fine displacement, which is smaller than the sampling interval, is calculated from the interpolated data.

Figure 2A:
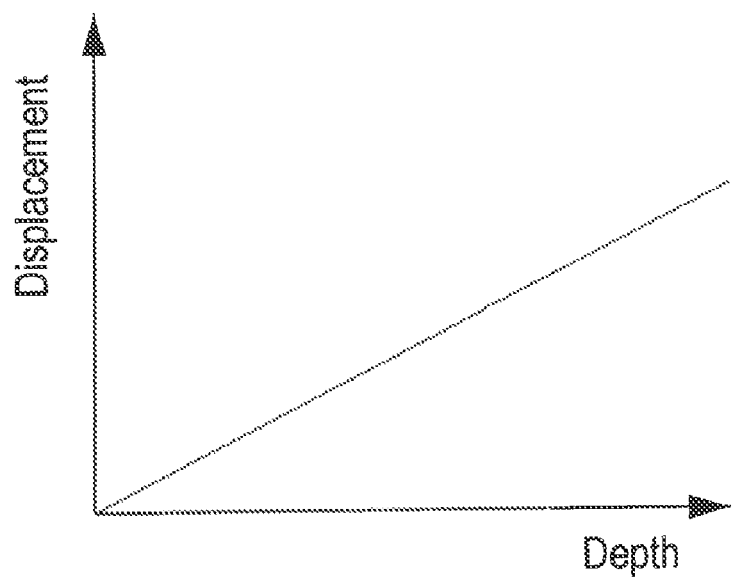
FIG. 2A is a graph showing a displacement of a tissue of a target object versus a depth when a pressure is applied thereto.
Figure 2B:
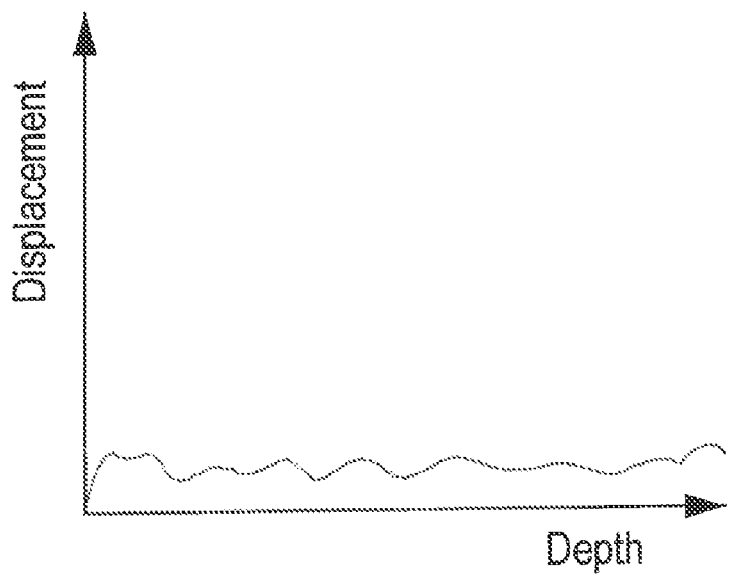
FIG. 2B is a graph showing a displacement versus a depth within a sampling interval in accordance with one embodiment of the present invention.
Figure 2C:
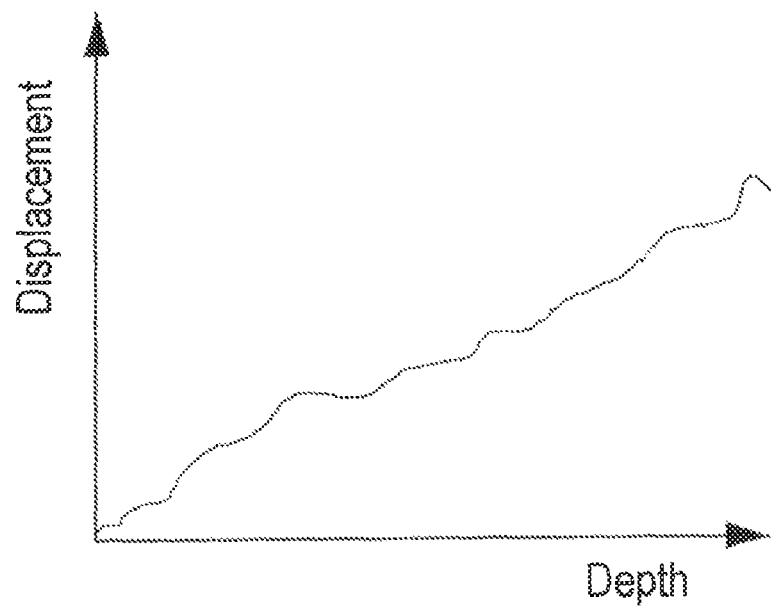
FIG. 2C is a graph showing a total displacement summing the coarse and fine displacements in accordance with one embodiment of the present invention.

FIG. 2A is a graph showing a coarse displacement versus a depth. FIG. 2B is a graph showing a fine displacement versus a depth in accordance with one embodiment of the present invention. A total displacement is determined by summing the coarse displacement and the fine displacement according to the stress applied. FIG. 2C is a graph showing the total displacement summing the coarse displacement and the fine displacement in accordance with one embodiment of the present invention.

Figure 3:
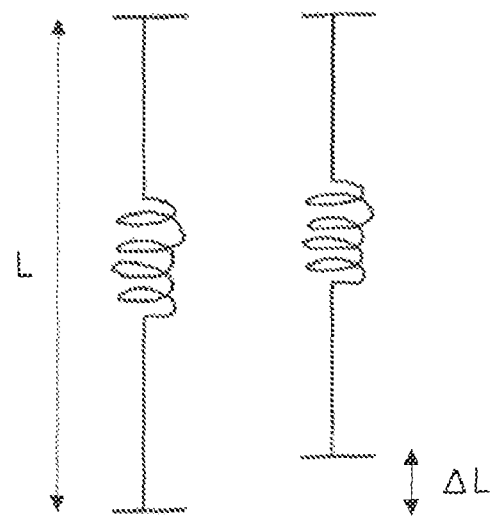
FIG. 3 shows a spring model for explaining a strain calculation.

When a stress is applied to the target object, the strain ($\epsilon$) in tissues of the target object may be calculated by using a spring model illustrated in FIG. 3, as shown in the following equation (1).

$$\epsilon = \Delta L/L \quad (1)$$

wherein "L" represents a length of the spring not applying the stress and "$\Delta L$" represents a length variation (displacement) of the spring according to the stress applied.

The strains may be calculated for respective scan lines by using a maximum displacement at each scan line in one frame of an elastic image. The calculated strains may be expressed as a graph visibly showing the strains for the respective scan lines. The strain graph may be displayed together with the elastic image in accordance with one embodiment of the present invention. Further, maximum displacements for the respective scan lines may be expressed as a graph in accordance with another embodiment of the present invention. The displacement graph may be displayed together with the elastic image.

Figure 4:
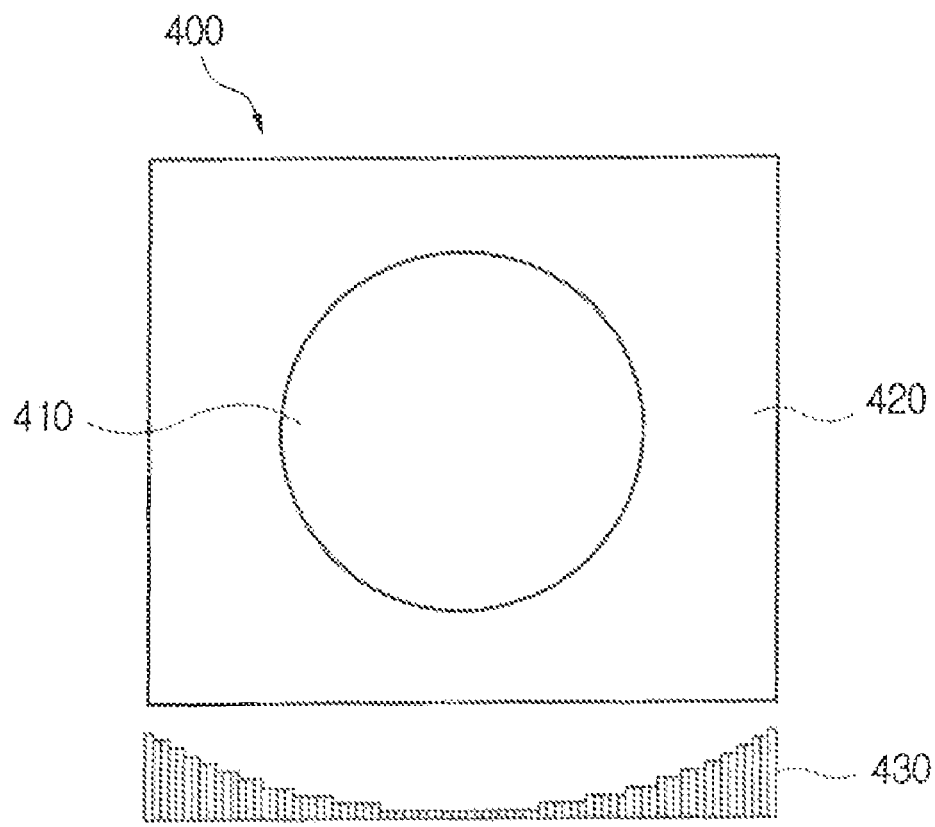
FIG. 4 is a schematic diagram showing an example of displaying an elastic image together with a strain graph in accordance with one embodiment of the present invention.

FIG. 4 shows an example of displaying an elastic image together with a strain graph showing strains for the respective scan lines. Referring to FIG. 4, the strain graph is displayed in a bar graph so as to visibly show strains for the respective scan lines in an elastic image 400. The elastic image shows that the target object has a relatively stiff tissue 410 and a relatively soft tissue 420. A portion corresponding to the stiff tissue 410 is illustrated in relatively short bars and a portion corresponding to the soft tissue 420 is illustrated in relatively long bars, as shown in FIG. 4.

In order to obtain an optimal elastic image, it is preferable that an average strain is maintained within a range of 0.5% to 3%. The average strain may be calculated by using the strains for the respective scan lines. The average strain may be displayed on a screen such that the average strain falls within a range of 0.5% to 3% by adjusting the stress.

Figure 5A:
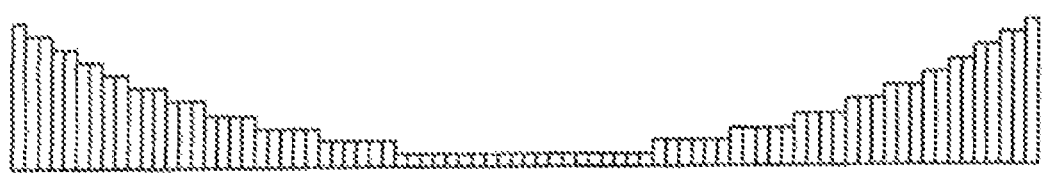
FIGS. 5A to 5E are diagrams showing examples of bar graphs illustrating strains for respective scan lines at each frame in accordance with one embodiment of the present invention.
Figure 5B:
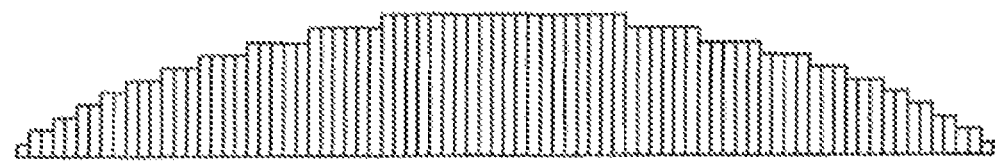
Figure 5C:
Figure 5D:
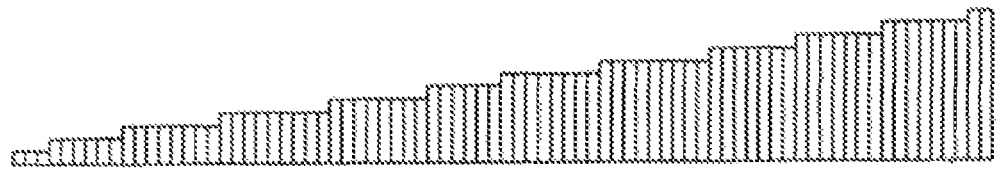
Figure 5E:
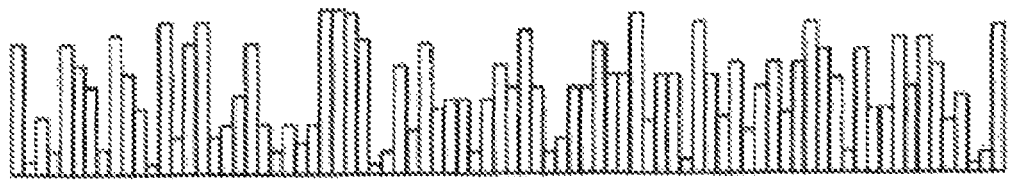
Figure 6A:
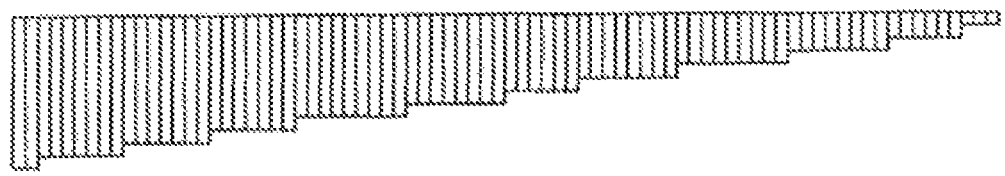
FIGS. 6A to 6D show examples of strain graphs in accordance with another embodiment of the present invention.
Figure 6B:
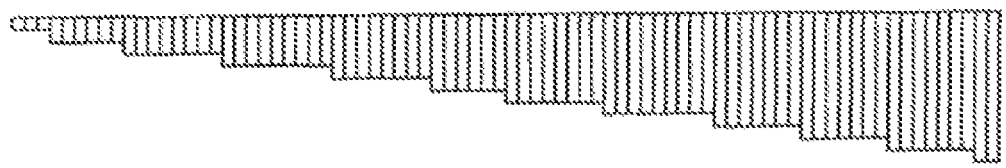
Figure 6C:
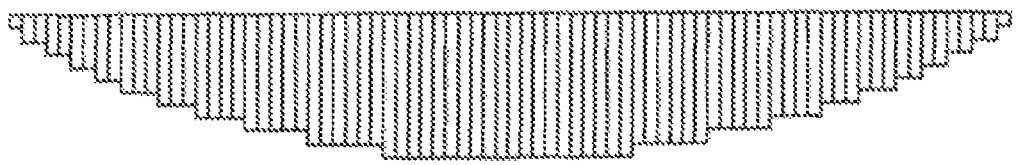
Figure 6D:
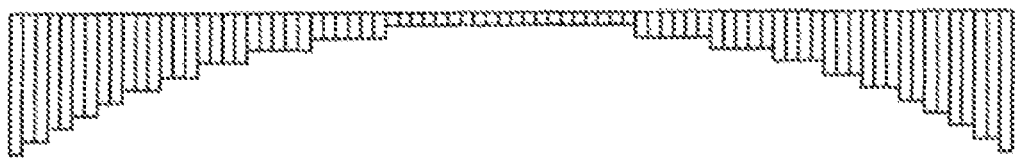

FIGS. 5A to 5E are graphs showing examples of bar graphs illustrating strains for the respective scan lines in one frame in accordance with one embodiment of the present invention. Referring to FIG. 5A, bars positioned at a center portion are short, while bars positioned at both edge portions are long. This means that a relatively stiff tissue exists at the center portion. Referring to FIG. 5B, it can be seen that a soft tissue exists at a center portion. FIG. 5C is a strain graph of an example showing that the stress applied to a left portion is harder than that applied to a right portion. On the contrary, FIG. 5D is a strain graph of an example showing that the stress applied to the right portion is harder than that applied to the left portion. FIG. 5E is a strain graph of an example showing incorrectly calculated strains for the respective scan lines. From FIG. 5E, it can be known whether an image process for obtaining an elastic image is correctly achieved through the strain graph.

A bottom side of the bar graph is fixed at an identical level and the strain bar at each scan line is indicated in an upward direction in accordance with one embodiment of the present invention. Also, a top side of the bar graph may be fixed at an identical level and the strain bar at each scan line may be indicated in a downward direction (shown in FIGS. 6A to 6D) in accordance with another embodiment of the present invention. Thus, the stress applied by the ultrasound probe can be instinctively recognized.

Further, when the stress is applied by using the ultrasound probe, it may be difficult to uniformly compress the target object due to a relatively small compression area of the ultrasound probe. That is, since the ultrasound probe has a finite compression area, the pressure may not be properly applied to a portion of the target object corresponding to an edge portion of the ultrasound probe compared to a portion of the target object corresponding to a center portion of the ultrasound probe. In such a case, since the pressure is not uniformly applied to the target object, it may affect the elastic image. Therefore, a normalization process for normalizing the strains for the respective scan lines is required to compensate for the non-uniform pressure due to the finite compression area of the ultrasound probe.

Further, if the stress is not uniformly applied to the target object, then the elastic image, which is displayed in real time, may deteriorate in terms of quality. Conventionally, a deteriorated frame in the elastic image is deleted or a previous frame of the deteriorated frame is repeatedly displayed such that the deteriorated frame is not displayed. In such a case, however, a problem arises in that screen flickers and the elastic image are not synchronized with a B-mode image. In order to solve the above problem, the present invention adopts an infinite impulse response (IIR) filter using the following equation (2).

$$Y_N = (1-P)Y_{N-1} + PX_N \quad (2)$$

wherein $Y_N$ represents a currently displayed frame in the elastic image, $Y_{N-1}$ represents a previous frame and $X_N$ represents a frame whose strains are currently calculated. P represents a persistence value ($0<P<1$). If P becomes large, then the weight of $X_N$ is increased in the currently displayed frame $Y_N$. On the other hand, if P becomes small, then the weight of $X_N$ is decreased in $Y_N$ so that the previous frame $Y_{N-1}$ is dominantly displayed in $Y_N$. The persistent P may be adjusted based on the average strain for each frame. If the average strain falls within a predetermined range (e.g., 0.5%-3%), then the persistent P is adjusted to be large such that the weight of $X_N$ is increased in $Y_N$. On the other hand, if the average strain is beyond the predetermined range, then the persistent P is adjusted to be small such that the previous frame $Y_{N-1}$ is dominantly displayed in $Y_N$. Therefore, an enhanced elastic image may be displayed in real time in accordance with one embodiment of the present invention.

Figure 7:
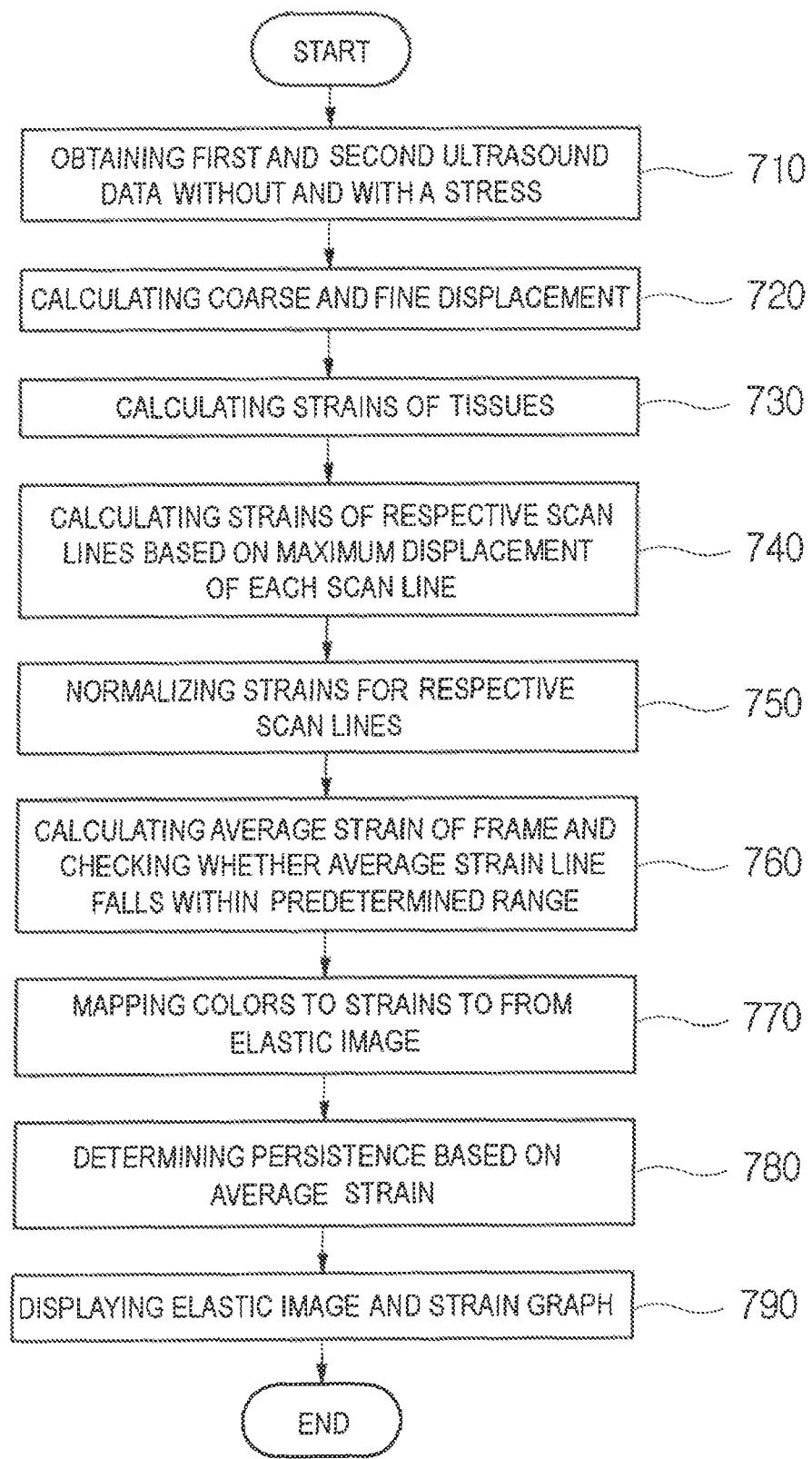
FIG. 7 is a flowchart showing a method of displaying an elastic image in accordance with one embodiment of the present invention.

FIG. 7 is a flowchart showing a method of displaying an elastic image in accordance with one embodiment of the present invention. Referring to FIG. 7, first ultrasound receive data are obtained before applying a stress. Then, second ultrasound receive data are obtained after applying a stress by transmitting an ultrasound signal to a target object at step S710. The first and second ultrasound receive data are compared to calculate first and second displacements at step S720. The first displacement is a coarse displacement calculated in a sampling interval unit by comparing the first ultrasound receive data and the second ultrasound receive data. The second displacement is a fine displacement, which is smaller than the sampling interval. After interpolating the first and second ultrasound receive data, the interpolated data are compared in order to calculate the second displacement. The first and second displacements are summed to calculate final displacements. Then, strains for tissues of the target object are calculated for forming an elastic image by using the final displacements at step S730. Thereafter, strains for the respective scan lines are calculated by using a maximum displacement among the final displacements at step S740.

The strains for the scan lines are normalized to reduce an effect upon the elastic image due to the non-uniform stress applied to the target object at step S750. After the normalization of the strains, an average strain is calculated at each frame and it is checked whether the average strain falls within a predetermined range (e.g., 0.5%-3%) at step S760. If it is determined that the average strain is beyond the predetermined range, then the stress applied to the target object is adjusted such that the average strain falls within the predetermined range. If the average strain falls within the predetermined range, then the ultrasound receive data and a graph showing the strains are mapped with preset colors at step S770.

Subsequently, the elastic image is filtered by the IIR filter wherein P is adjusted to prevent the quality of an elastic image from being deteriorated due to the non-uniform stress at step S780. The filtered elastic image and the color-mapped graph are displayed at step S790.

Figure 8:
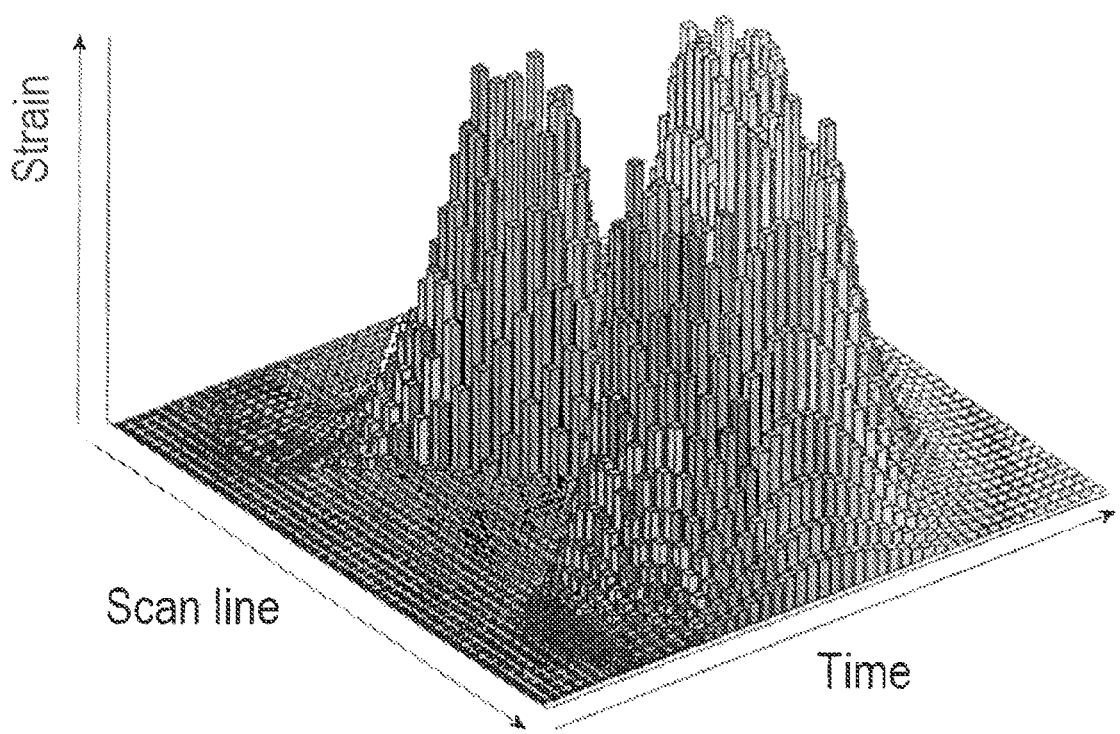
FIG. 8 is a graph three-dimensionally showing a strain graph extended to a time axis in accordance with one embodiment of the present invention.
Figure 9:
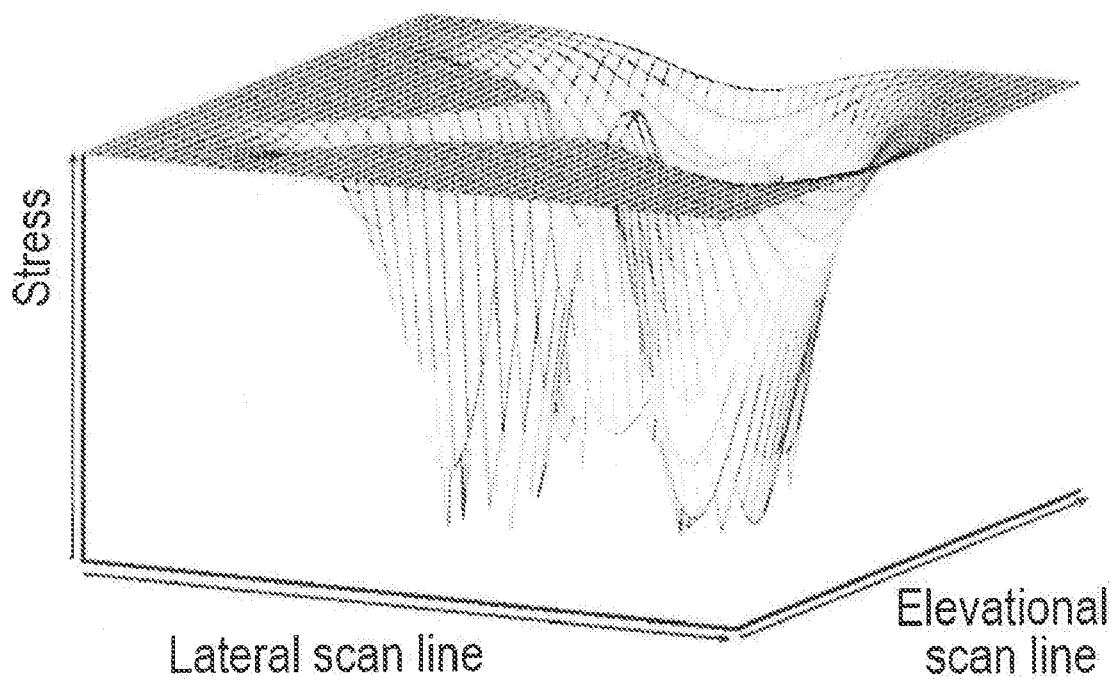
FIG. 9 is a graph three-dimensionally showing stresses applied by using an ultrasound probe employing a two-dimensional transducer array for all scan lines.

While the graph showing the strains for the respective scan lines is displayed in a two-dimensional graph in accordance with one embodiment of the present invention, the graph may be three-dimensionally displayed on a time axis (shown in FIG. 8) in accordance with another embodiment of the present invention. As the strain graph is displayed as shown in FIG. 8, the changes in the strains can be displayed along the time axis. FIG. 9 is a graph three-dimensionally showing the stresses for all scan lines when a two-dimensional transducer array in the ultrasound probe is adopted. Although the bar graph is used as an example of the graph for showing the displacements or the strains for the respective scan lines in accordance with one embodiment of the present invention, any type of graph such as a line graph capable of showing the displacements or the strains for the respective scan lines may be used.

As mentioned above, since the strain graph showing the strains for the respective scan lines is displayed together with the elastic image in accordance with the present invention, the average strain can be easily calculated at each frame of the elastic image displayed in real time. Therefore, the stress can be adjusted such that the average strain falls within the predetermined range. Further, as the persistence value P is adjusted at the IIR filter according to whether the average strain falls within the predetermined range, an optimized elastic image can be outputted.

Also, an elastic characteristic of the target object can be visibly recognized through the shape of the strain graph. Further, the stress can be uniformly applied to the target object without leaning the stress toward one way.

A method of displaying an elastic image comprises the following steps: a) performing transmission/reception of an ultrasound signal along a plurality of scan lines set on a target object to obtain first ultrasound data, the target object including a plurality of tissues; b) performing transmission/reception of an ultrasound signal along a plurality of scan lines set on the target object by applying a stress to the target object to obtain second ultrasound data; c) calculating displacements of the tissues based on the first and second ultrasound data; d) calculating strains in the tissues based on the calculated displacements; e) forming an elastic image based on the calculated strains and a graph indicating changes of the tissues for the respective scan lines; and f) displaying the elastic image together with the graph.

Any reference in this specification to "one embodiment," "an embodiment," "example embodiment," etc., means that a particular feature, structure or characteristic described in connection with the embodiment is included in at least one embodiment of the present invention. The appearances of such phrases in various places in the specification are not necessarily all referring to the same embodiment. Further, when a particular feature, structure or characteristic is described in connection with any embodiment, it is submitted that it is within the purview of one skilled in the art to effect such feature, structure or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A method of displaying an elastic image, comprising:
 a) performing transmission/reception of an ultrasound signal along a plurality of scan lines set on a target object to obtain first ultrasound data, the target object including a plurality of tissues;
 b) performing transmission/reception of an ultrasound signal along a plurality of scan lines set on the target object while applying stress to the target object to obtain second ultrasound data;
 c) calculating, with a processor, displacements of the tissues at the respective scan lines based on the first and second ultrasound data;
 d) calculating, with a processor, strains at the respective scan lines based on the calculated displacements and average strains of the strains for the respective scan lines;
 e) forming an elastic image based on the calculated strains and a graph indicating the average strains at the respective scan lines; and
 f) displaying the elastic image together with the graph.

2. The method of claim 1, further comprising:
forming a displacement graph indicating a maximum displacement at each scan line and displaying the elastic image together with the displacement graph.

3. The method of claim 1, wherein the step c) includes:
c1) comparing the first and second ultrasound data to calculate a first displacement in a sampling interval unit;
c2) interpolating the first and second ultrasound data;
c3) comparing the interpolated first and second ultrasound data to calculate a second displacement smaller than a sampling interval; and
c4) summing the first and second displacements to calculate the displacement.

4. The method of claim 3, further comprising step d1) of normalizing strains for the respective scan lines based on strains calculated at step d).

5. The method of claim 4, further comprising:
d2) calculating the average strain of each scan line;
d3) checking whether the average strain falls within a predetermined range; and
d4) if it is determined that the average strain does not fall within the predetermined range, then adjusting the stress applied to the target object.

6. The method of claim 2, wherein at the step e), colors preset to respective displacements are mapped to the calculated displacements to form the elastic image.

7. The method of claim 1, wherein at the step e), colors preset to respective strains are mapped to the calculated strains to form the elastic image.

8. The method of claim 1, wherein the graph is one of a bar graph and a line graph.

9. The method of claim 8, wherein the elastic image is filtered with an infinite impulse response filter, a persistence of which is adjusted according to the average strain.

* * * * *